United States Patent [19]

Greenstone

[11] Patent Number: 5,656,437
[45] Date of Patent: Aug. 12, 1997

[54] **MONOCLONAL ANTIBODY TO VITELLIN OF THE CORN EARWORM, *HELICOVERPA ZEA***

[75] Inventor: Matthew H. Greenstone, Columbia, Mo.

[73] Assignee: The United States of America as represented by the Secretary of Agriculture, Washington, D.C.

[21] Appl. No.: 499,803

[22] Filed: Jul. 7, 1995

[51] Int. Cl.$^6$ .................................................. G01N 33/53
[52] U.S. Cl. ........................ 435/7.1; 435/7.92; 435/189; 514/12; 554/83
[58] Field of Search ........................ 435/7.1, 189, 7.92; 514/12; 554/83

[56] References Cited

PUBLICATIONS

Greenstone et al, Annals of the Entomalogical Soc. of Am. vol. 87(2) Mar. 1994, pp. 214–217.
Shaw, Cotton Pesticides Guide, 1993–1994, NSW Agriculture Austrialian Cotton Research Institute, Ed. by E. Roberts.
Forrester, Nell, et al., "Insecticide Resistance Management Strategy for Heliothis 1993–94", *Cotton Pesticides Guide 1993–94*, NSW Agriculture, Australian Cotton Research Institute, RMB Myall Vale, Narrabri, NSW 2390, pp. 8–13.

Greenston, Matthew H., "Bollworm or Budworm? Sqashbt Immunoassay Distinguishes Eggs of *Helicoverpa Zea* and *Heliothis virescens* (Lepidoptera: Noctuidae)", *Journal of Economic Entomology*, vol. 88, No. 2, Apr. 1995, pp. 213–218.
Greenstone, Matthew and Trowell, Stephen C., "Arthropod Prediation: A Simplified Immunodot Format for Predator Gut Analysis", *Annals of the Entomological Soc. of America*, vol. 87, No. 2, Mar. 1994, pp. 214–217.
Lenz, Cynthia L. and Greenstone, Matthew H., "Production of a Monoclonal Antibody to the Arylphorin of *Heliothis zea*", *Archives of Insect Biochemistry and Physiology*, 1988, pp. 167–177.

*Primary Examiner*—James C. Housel
*Assistant Examiner*—Ginny Allen Portner
*Attorney, Agent, or Firm*—M. Howard Silverstein; Randall E. Deck; John D. Fado

[57] ABSTRACT

A hybridoma cell line is described which produces and secretes a monoclonal antibody which specifically binds to vitellin in the eggs of the corn earworm, *Helicoverpa zea*, but does not bind to vitellin in the eggs of the tobacco budworm, *Heliothis virescens*. Eggs of *H. zea* may be detected and differentiated from eggs of *H. virescens* by subjecting a sample of insect eggs to an immunosorbent assay using the above-mentioned monoclonal antibody. The monoclonal antibodies may also be incorporated into kits for the detection of eggs of *H. zea* in the field.

8 Claims, No Drawings

MONOCLONAL ANTIBODY TO VITELLIN OF THE CORN EARWORM, *HELICOVERPA ZEA*

BACKGROUND OF THE INVENTION

1. Field of the Invention

This invention relates to a hybridoma cell line and monoclonal antibody produced thereby which may be used to detect eggs of the corn earworm, *Helicoverpa zea*.

2. Description of the Prior Art

Both the corn earworm (also known as the cotton bollworm), *Helicoverpa zea*, and the tobacco budworm, *Heliothis virescens*, infest cotton fields in Texas, midsouth United States, and Mexico. If uncontrolled, these two species, commonly referred to as the budworm/bollworm complex, have the potential to inflict very substantial yield losses at harvest. However, efforts to control the insects have been hampered by the tendency of the budworm, *H. virescens*, to become resistant to pyrethroid insecticides. As yet, the corn earworm, *H. zea*, has not exhibited resistance to pyrethroids.

Pyrethroid resistance in *H. virescens* in cotton was first detected in California in the early 1980s and in the midsouth and in Texas in the mid 1980s (Gage et al., 1991, Intro. Southwest. Entomol. Suppl., 15:1–3), and has increased in intensity in several regions during subsequent years (Carillo, 1991, Proceedings, Beltwide Cotton Production Res. Conference, Nashville, Tenn., Jan. 2–7, 1989, National Cotton Council of America, Nashville, Tenn., pp. 59–67; Elzen et al., 1991, Southwest. Entomol. Suppl., 15:27–31; and Graves et al., 1991, Southwest. Entomol. Suppl., 15:33–41).

Levels of pyrethroid resistance vary temporally and geographically, tending to begin low and increase during the growing season, and to be higher in cotton growing than in noncotton growing areas (Graves ibid; Lettrell et al., 1991, Southwest. Entomol. Suppl., 15:5–26; and Plapp, 1991, Southwest. Entomol. Suppl., 15:69–73). These trends indicate not only that the evolution of resistance is promoted by pyrethroid use, but that when selection pressure is relaxed, genes for pyrethroid resistance confer reduced fitness. This interpretation is supported by laboratory studies demonstrating reduced female attractiveness, reduced fecundity, and increased development times in resistant populations (Campanhola and Plapp, 1989, Proceedings, Beltwide Cotton Production Res. Conference, Nashville, Tenn., Jan. 2–7, 1989, National Cotton Council of America, Nashville, Tenn., pp. 352–359; and McCutcheon et al., 1989, Proceedings, Beltwide Cotton Production Res. Conference, Nashville, Tenn., Jan. 2–7, 1989, National Cotton Council of America, Nashville, Tenn., pp. 364–366). Hence a reduction of pyrethroid use can be expected to retard the development of resistance and extend the useful life of these chemicals (Mallett and Luttrell, 1991, Southwest. Entomol. Suppl., 15:201–212).

Because cotton fields may be infested with either or both of *H. zea* or *H. virescens*, control efforts, particularly the selection of an appropriate pesticide and the amount applied, would be aided by the ability to accurately differentiate between these two closely related pests at an early stage, preferably as eggs. However, there are currently no means available for readily differentiating between eggs of *H. zea* and *H. virescens* in the field. This has often resulted in the wasteful spraying of pyrethroids as well as the overexposure of populations of *H. virescens* to the insecticides, thereby increasing selection pressure for pyrethroid resistance. Unnecessary spraying also depresses natural enemy populations, further hindering control of infestations. Morphological differences between eggs of *H. zea* and *H. virescens* were described by Bernhardt and Phillips (1985, Southwest. Entomol., 10:236–238). However, these differences have proved too subtle to be practical for wide scale use in field determinations.

Immunoassays employing monoclonal antibodies have been developed as tools in ecological studies involving predator-prey relationships. This approach has been used to evaluate predators as potential biocontrol agents. In these studies, digestive tract contents of potential predators are subjected to immunochemical analysis to determine if they have ingested specific pest insects. One such monoclonal antibody binding the arylphorin of *H. zea*, which was produced to whole plasma of the fifth instar larvae of *H. zea*, was described by Lenz and Greenstone (1988, Arch. Insect Biochem. Physiol., 9:167–178) and Greenstone and Morgan (1989, Ann. Entomol. Soc. Am., 82:45–49). Hagler (1994, Ann. Entomol. Soc. Am., 87:85–90) described a monoclonal antibody specific for an egg antigen of the pink bollworm, *Pectinophora gossypiella* (Saunders). Most recently, Greenstone and Trowell (1994, Ann. Entomol. Soc. Am., 87:214–217) described two additional monoclonal antibodies produced using the purified vitellins of *H. virescens* and *H. zea*, respectively, as immunogens. Vitellins have been previously described as the major yolk proteins of insect eggs, including Lepidopterans such as *H. zea* and *H. virescens* by Hagedorn and Kunkel (1979, Ann. Rev. Entomol., 24:475–505), Harnish and White (1982, J. Exp. Zool., 220:1–10), Kunkel and Nordin [1985, Yolk Proteins, In: Comprehensive Insect Physiology, Kerkut and Gilbert (eds.), Pergamon Press, Oxford, vol. 1, pp. 83–111], Kanost et al. (1990, Adv. Insect Physiol., 22:299–396), and Raikhel and Dhadialla (1992, Ann. Rev. Entomol., 37:217–251). However, while the monoclonal antibodies of Greenstone and Trowell were prepared against the vitellins of *H. zea* and *H. virescens*, they recognize the eggs of heliothine noctuid insects in general, and they cannot differentiate between the species, nor can they differentiate between the eggs of *H. zea* or *H. virescens*.

SUMMARY OF THE INVENTION

I have now discovered a hybridoma cell line which produces and secretes a monoclonal antibody which specifically binds to vitellin in the eggs of the corn earworm, *Helicoverpa zea*, but does not bind to vitellin in the eggs of the tobacco budworm, *Heliothis virescens*. By subjecting a sample of insect eggs to an immunosorbent assay using the above-mentioned monoclonal antibody, eggs of *H. zea* may be readily detected and differentiated from eggs of *H. virescens*. The monoclonal antibodies may also be incorporated into kits for the detection of eggs of *H. zea* in the field.

It is an object of this invention to provide a hybridoma cell line which produces a monoclonal antibody which specifically binds to eggs of the corn earworm, *H. zea*, and does not bind to eggs of the tobacco budworm, *H. virescens*.

It is another object of this invention to provide monoclonal antibodies useful as immunochemical reagents for the early detection of infestations of *H. zea* on agronomically important crops.

Other objects and advantages of the invention will become apparent from the ensuing description.

DETAILED DESCRIPTION OF THE INVENTION

In accordance with this invention, I have created a hybridoma cell line that produces and secretes a monoclonal antibody which selectively binds to the vitellin of the corn earworm (cotton bollworm), *Helicoverpa zea*, but does not bind to the vitellin of the tobacco budworm, *Heliothis virescens*. The antibody, which has been designated HZE-1, possesses greater specificity than the previously described monoclonal antibodies to the vitellins of *H. zea* or *H. virescens* (Greenstone and Trowell, 1994, ibid) which are unable to differentiate between eggs of these pests. Moreover, the antibody exhibits a high degree of sensitivity to the vitellin of *H. zea*, enabling the detection of small amounts of egg or egg homogenates by immunoassay.

In contrast to the earlier hybridoma cell lines of Greenstone and Trowell (1994, ibid) which were prepared using purified *H. zea* and *H. virescens* vitellin as immunogens, the hybridoma cell line of this invention was generated using the soluble fraction of *H. zea* whole egg homogenate as immunogen. Hybridoma production, including the steps of immunizing an animal with the immunogen, recovering spleen lymphocytes therefrom, and fusing the splenocytes with continuously replicating myeloma cells to produce hybrid cells, was conducted using conventional techniques, as described by Lenz and Greenstone (1988, ibid, the contents of which are incorporated by reference herein). Hybridoma supernatants were screened for production of antibodies by indirect ELISA with *H. zea* whole egg homogenate as antigen.

One monoclonal antibody, designated HZE-1, exhibited a high affinity for eggs of *H. zea*, with ELISA absorbances more than five times above the background. Surprisingly, when examined for specificity to a plurality of noctuid eggs, particularly eggs of *H. virescens*, monoclonal antibody HZE-1 was specific for eggs of *H. zea* and did not bind to eggs of *H. virescens* nor other noctuids which may infest cotton in North America.

The hybridoma cell line which produces and secretes monoclonal antibody HZE-1, has been deposited under the Budapest Treaty in the American Type Culture Collection, Rockville, Md., on Jun. 8, 1995, and has been assigned accession number ATCC HB 11941.

Large quantities of monoclonal antibody HZE-1 may be produced by propagation of the hybridoma using well-known tissue culture techniques. Alternatively, antibody may be produced within host animals, such as by ascites formation in syngenic mice. Monoclonal antibodies so produced may be purified, for example, by affinity chromatography on a protein A or G resin, or using *H. zea* vitellin bound to a resin.

Monoclonal antibody HZE-1 may be used to rapidly and accurately detect eggs of *H. zea* on plant surfaces, providing an early indicator of crop infestation, particularly in cotton. The eggs are the preferred stage of detection because they are typically deposited near the tops of cotton plants, where they are easily sampled. In contrast, once hatched, larvae quickly enter the squares and bolls where they become inaccessible and difficult to sample. Moreover, with the proper identification of eggs of *H. zea* or *H. virescens*, management strategies may be implemented which avoid the application of inappropriate insecticides, particularly pyrethroids.

Eggs of *H. zea* in unknown samples may be detected using monoclonal antibody HZE-1 in conjunction with a variety of well-known immunosorbent assay procedures, including but not limited to RIA, fluorescent immunoassay, or ELISA. However, in a preferred embodiment, eggs of *H. zea* may be detected by squashblot immunoassay. In accordance with this technique, samples suspected of containing eggs are collected, such as by brushing or rinsing plant leaves, and transferred to the surface of a solid substrate, preferably a membrane. While it is envisioned that the membrane may be constructed from a number of different materials, nitrocellulose membranes are particularly preferred. Optionally, to provide a reference for the placement of egg samples, a transparent or translucent membrane may be placed over a matrix of dark spots, or the membrane itself may be provided with spots identifying sample areas. Once on the substrate or membrane, the eggs are squashed or crushed, allowed to dry, and then incubated with monoclonal antibody HZE-1. Following incubation the surface is washed and bound antibody on the membrane detected. Suitable reagents for detection of bound antibody are known in the art, and include, but are not limited to detectably labeled anti-immunoglobulins or preferably anti-mouse biotin with detectably labeled Streptavidin. Preferred labels which may be used herein include fluorescent labels and enzyme/substrate labels as are conventional in the art.

In an alternative embodiment, eggs of *H. zea* may be determined by a competition ELISA such as described in Brandon et al. (U.S. Pat. No. 5,053,327, the contents of which are incorporated by reference herein), using the monoclonal antibody of the invention attached to a solid support. For example, the HZE-1 antibody may be immobilized on a bead or in a microtiter well. The unknown sample to be analyzed containing crushed or homogenized eggs are then added together with enzyme-, fluorescent-, or radiolabeled *H. zea* vitellin, and the amount of labeled vitellin bound to the antibody is then measured, using a substrate when the label is an enzyme. The amount of vitellin or eggs of *H. zea* in the sample is inversely proportional to the amount of bound labeled vitellin. In another alternative, it is also envisioned that the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. Such a kit for use herein comprises a first container comprising the monoclonal antibody, and a second container comprising a detection reagent effective for detecting bound antibody. A substrate or membrane for receiving the sample material may also be incorporated into the kit.

Using the monoclonal antibody HZE-1 of this invention, eggs of *H. zea* may be detected on a variety of agronomically important crops, including but not limited to cotton, beans, tomatoes, and corn.

Monoclonal antibody HZE-1 may have other applications as well. For example, the antibody may be used as a tool to monitor insect pest populations for directing insecticide applications and evaluating control measures. Further still, the antibody may be used for predator gut analysis, such as described by Greenstone and Trowell (1994, ibid, the contents of which are incorporated by reference herein) to identify predators of *H. zea* as potential biocontrol agents.

A detailed description of monoclonal antibody HZE-1 and procedures for its use to detect eggs of *H. zea* is provided in Greenstone (1995, J. Econ. Entomol., 88:213–218), the contents of which are incorporated by reference herein.

The following examples are intended only to further illustrate the invention and are not intended to limit the scope of the invention which is defined by the claims.

EXAMPLE 1

Hybridoma and Monoclonal Antibody HZE-1 Production

Immunization

Eggs of *H. zea* were obtained from colonies maintained in continuous culture at the Biological Control of Insects Research Laboratory (BCIRL) in Columbia, Mont., using established rearing methods (Berger, 1963, USDA Agric. Res. Serv. pub. ARS-33-84:1–4; Ignoffo, 1965, J. Invertebr. Pathol., 7:217–226; and Ignoffo and Boening, 1970, J. Econ. Entomol., 63:1696–1697). Whole eggs were homogenized in PBS in a tissue grinder, and the water soluble fraction (referred to as the egg homogenate) was recovered for use as immunogen.

BALB/c mice were injected intraperitoneally (IP) with 0.25 ml of an emulsion containing equal quantities of Freund's Complete Adjuvant (Gibco, Grand Island, N.Y.) and 100 µg of the above-mentioned egg homogenate. The mice received two booster IP injections of the 100 µg of the egg homogenate without adjuvant at 3-week intervals. Four days prior to fusion the mice received a final injection of 80 µg of egg homogenate via a tail vein.

Mice were anesthetized, killed by exsanguination, and splenectomized. Splenocytes were fused with SP2/0 myeloma cells by established protocol (Nahm et al., 1982, J. Immunol., 129:1513). Fused cells were resuspended in HAT medium and plated out into the wells of 96-well plates and kept at 37° C. in an atmosphere of 8.5% $CO_2$. The cells were fed by replacing half the medium with new HAT three times a week until all wells that showed growth had been screened. Seven such fusions were performed yielding a total of 340 hybridomas. Hybridoma supernatants were analyzed by indirect ELISA for the presence of antibodies against egg homogenate.

Indirect ELISA for hybridoma selection

Indirect ELISAs were performed in disposable 96-well EIA plates (Costar, Cambridge, Mass.), and 0.1 ml of each reagent was used in each step. Except as noted, all incubations were performed at 37° C. for 30 min with rotation at 100 rpm on a Mini-Orbital Shaker (Bellco, Vineland, N.J.). Between reagents the plates were washed four times in rapid succession with tapwater containing 0.05% Tween 20 (Fisher Scientific, Fair Lawn, N.J.) and blotted on paper towels. Wells were coated with 100 µg/ml of the egg homogenate as antigen and incubated. Nonspecific binding was decreased by blocking the wells with 20% BLOTTO (Johnson et al., 1984, Gene Anal. Technol., 1:3) in PBS and incubated for 15 min. After washing, undiluted hybridoma supernatants were added and allowed to bind to the coated microwells. After removal of unbound antibody by washing, anti-mouse IgG-alkaline phosphatase conjugate (Sigma) diluted 1:500 in PBS containing 0.05% Tween-20 and 0.5% BSA was added to each well. After incubation, substrate p-nitrophenyl phosphate at 1.0 mg/ml was added and incubated 30 min without rotation at 25° C. Bound antibody was determined by measuring the absorbance of each well at 405 nm using a Titertek Multiscan ELISA plate reader (Flow Laboratories, McLean, Va.). A total of nine hybridomas produced monoclonal antibodies which recognized the immunizing antigen at an ELISA absorbance level at least three times above background.

Hybridoma expansion

The nine hybridomas eliciting the highest absorbances during ELISA were cloned twice by limiting dilution [McKearn, 1980, Cloning of hybridoma cells by limiting dilution in fluid phase, In: Monoclonal Antibodies, Kennet et al. (eds), Plenum Press, N.Y., p. 374] with 50% SP2/0-conditioned medium in place of thymocytes. Three of the nine hybridomas were successfully cloned, and all were specific for *H. zea* egg homogenate only. One of these gave ELISA absorbances more than five times above the background, and was retained. This monoclonal antibody was designated HZE-1.

Antibodies were produced by mass tissue culture in Nutridoma serum-free medium (Boehringer-Mannheim, Indianapolis, Ind.), concentrated by ultrafiltration and treatment with Aquacide (Calbiochem, La Jolla, Calif.) to at least 10.0 mg/ml, and stored at −80° C.

EXAMPLE 2

Immunoassay for evaluating sensitivity and specificity

A squashblot immunoassay was used to determine the sensitivity and specificity of the monoclonal antibody HZE-1 for binding eggs of *H. zea*. In the initial experiments eggs of *H. zea* and *H. virescens* were obtained from colonies maintained at the BCIRL laboratory as described in Example 1.

Assay Protocol

Assays were performed on reinforced nitrocellulose membranes (Hybond-C Super, Amersham, Arlington, Ill.). For each assay, a membrane was cut to appropriate size and taped over a vinyl-jacketed 8×12 matrix of darkly photocopied, spaced dots; the dots, visible through the translucent membrane, provided reference for the placement of individual 1.0 µl spots of egg homogenate or individual eggs (after placement eggs were squashed and allowed to dry). After a minimum of 15 min for drying, the membrane was blocked for 1 hr in 5.0% BLOTTO (see Example 1) containing 5.0 mg/ml protease IV (Sigma, St. Louis, Mo.), to prevent non-specific binding and inhibit endogenous peroxidases. Blocking with protease IV is preferred, as this reagent reduces non-specific reactions by *H. virescens* without degrading signal strength of *H. zea* eggs. Although residual protease may cause casein coagulation in the antibody incubation step, eggs of *H. zea* are nonetheless readily distinguishable from those of other species. We have also found while other blockers of endogenous peroxidases may be used, such as phenylhydrazine as described by Greenstone and Trowell (1994, ibid), eggs of *H. virescens* may occasionally appear as weak false positives. Following blocking, the membrane was then washed six times in rapid succession with tap water.

The remaining reagents were then added serially, each incubated for 30 min at 37° C. with rotation, followed by six rapid washes in tap water, as follows: 25, 50 or 100 µg/ml of monoclonal antibody HZE-1 in BLOTTO containing 10% newborn calf serum (NBCS)(Sigma); 1:1,000 sheep anti-mouse biotin in 2% NBCS in BLOTTO; and 1:1,500 Streptavidin peroxidase in 2% NBCS in PBS at pH 7.4.

After the final wash, the substrate, 3-amino-9-ethyl-carbazole (Graham et al., 1965, J. Histochem. Cytochem., 13:150–152), was added and the membrane rotated for 3 min by hand at room temperature. The reaction was stopped by rinsing twice briefly in distilled water and then twice more in distilled water for 2 min with rotation each time.

Assay Sensitivity

Assay sensitivity was determined using two-fold serial dilutions from 1.0 µg to 1.0 ng protein of egg homogenate from Example 1. One µl of each homogenate was placed over a dot, and assayed as described above.

The assays detected the same amount of *H. zea* egg homogenate protein at all three antibody concentrations tested, 125 ng.

Antibody/Assay Specificity

Tests of antibody and assay specificity were conducted using eggs from *H. zea* and *H. virescens*, and other noctuids occasionally found on cotton: *Heliothis sublexa* (Grote), *Spodoptera frugiperda* (J. E. Smith), *Trichoplusia ni* (Hübner), and *Anticarsia gemmatalis* (Hübner). Individual eggs from long-term BCIRL moth colonies were obtained from insectary egg sheets (paper towels) or from soybean or cotton leaves exposed to adult moths in a rearing chamber. Infertile *H. zea* eggs were obtained by exposing soybean leaves to virgin females. Eggs from egg sheets were loosened by immersion in tap water, whereas those from leaves were removed with an artist's brush. The brush was used to position individual eggs over the spots seen through the nitrocellulose membrane. Each egg was then squashed in place with a 2.5 mm diameter wooden applicator stick (Abco, Milwaukee, Wis.). The completed membrane was allowed to dry and then assayed as described above, with the concentration of monoclonal antibody HZE-1 set at 25 µg/ml. Eggs squashed on the membrane sometimes left a permanent brownish residue regardless of species. However, only *H. zea* eggs produced a positive result: a large pink spot in the assay.

The results are shown in Table 1. More than 2,500 insectary-reared eggs were tested. Five of 1,269 *H. zea* eggs were negative, giving a false negative rate of 0.4%; one of 1,157 *H. virescens* eggs was positive for a false positive rate of 0.1%. All tested eggs of the other four noctuid species were negative. *S. frugiperda* eggs tended to melanize intensely, but the resulting inky black spots were easily distinguishable from the large pink spots of *H. zea* positives.

To ensure that species specificity was not limited to laboratory stock cultures, the squashblot assay described above was repeated using eggs produced by *H. zea* and *H. virescens* collected from widely distributed field populations. Larvae or adults were identified to species and collected from cotton and corn fields in Tift County, Ga., Washington County, Miss., Fayette County, Tenn., and Burleson and Hidalgo counties, Tex. Both species were collected at the Tift County, Ga., site, while *H. virescens* were collected from all sites. The adults were mated and the resulting eggs were transported to the laboratory and assayed as described above. Larvae were allowed to pupate and the pupae were also sent to the laboratory where they were permitted to eclose, mate, and oviposit. These eggs were also collected and assayed as above. The results are shown in Table 2. All but one *H. zea* egg were positive, and all *H. virescens* eggs were negative.

EXAMPLE 3

Antibody characterization

The antigenic determinants of monoclonal antibody HZE-1 and monoclonal antibody HVE-1 of Greenstone and Trowell (1994, ibid) were identified by western blot analysis using purified *H. zea* and *H. virescens* vitellins and preparations of a variety of noctuid insects.

Sample preparation

Purified *H. zea* and *H. virescens* vitellins were kindly provided by N. Haunerland, Dept. Biol. Sci., Simon Fraser Univ., Burnaby, B. C., Canada. All new world insects [*H. zea*, *H. virescens*, *Heliothis subflexa* (Grote), *Spodoptera frugiperda* (J. E. Smith), *Trichoplusia ni* (Hübner), and *Anticarsia gemmatalis* (Hübner)] were obtained from laboratory colonies reared on artificial diets as described in Example 1. The Old World heliothines [*Helicoverpa armigera* (Hübner), and *Helicoverpa punctigera* (Wallengren)], were kindly provided by S. C. Trowell, Division of Entomology, CSIRO, Canberra, Australia. Samples for antigen characterization were prepared from eggs, whole first and second instars, and fifth instar, pupal and adult hemolymph. Whole egg and larval homogenates were generated by maceration in a tissue grinder containing PBS as described by Lenz and Greenstone (1988, ibid). Hemolymph from fifth instars was collected from proleg incisions as described by Lenz and Greenstone (1988). Hemolymph from pupae and adults was collected using a modification of the technique of Satyanarayana et al. (1992, Invertebr. Reprod. Devel., 21:169–178). Specimens were decapitated, placed into 1 ml disposable syringes, and centrifuged in 15 ml centrifuge tubes containing 1 µl 3 mM 1-phenyl-2-thiourea (200×g, 10 min, 4° C.). The hemolymph was removed from the tubes, pooled, and centrifuged at 12,000×g at 4° C. for 3 min to remove debris. Protein concentrations of the samples were determined by a dye-binding method (Bradford, 1976, Anal. Biochem., 72:248–254) using bovine serum albumin as the standard (Bio-Rad Laboratories, Inc., Hercules, Calif.).

Monoclonal antibodies

Two monoclonal antibodies to eggs of *H. zea* and *H. virescens* were examined. The first of these was monoclonal antibody HZE-1 of Example 1. The second, monoclonal antibody HVE-1, was prepared using the purified vitellin of *H. virescens* as immunogen, as described by Greenstone and Trowell (1994, ibid).

Western blotting

Denaturing and nondenaturing PAGE were performed using the PhastSystem (Pharmacia LKB Biotechnology, Inc., Piscataway, N.J.). Electrophoretic gels with acrylamide gradients were used in both procedures (SDS-PAGE, 10–15%; native PAGE, 4–15%; 4.5%T, 3%C; 0.45 mm) (Laemmli, 1970, Nature, 227:680–685; Slater, 1969, Anal. Chem., 41:1039–1041; PhastSystem Separation Technique File Nos. 110 and 130), with each lane containing 3.3–10.7 µg protein. Proteins were stained with 0.1% Coomassie blue R350 (PhastSystem Development Technique No. 200). Molecular weight standards included *H. zea* arylphorin (provided by N. Haunerland, Dept. Biol. Sci., Simon Fraser Univ., Burnaby, B. C., Canada) and commercially prepared purified proteins (Pharmacia LKB Biotech., Inc.)

Proteins from PAGE were blotted onto nitrocellulose according to Towbin et al. (1979, PNAS U.S.A., 76:4350–4354) using the PhastTransfer semi-dry electrophoretic transfer system (Pharmacia LKB Biotech., Inc.). After protein transfer was complete, the membranes were processed using a modification of the technique of Greenstone and Trowell (1994). Membranes were incubated in blocking solution (5% non-fat dry milk, Bio-Rad Laboratories, Inc., in TBS) for 30 min at 37° C. with constant rotation, and washed six times in rapid succession with deionized water. The membranes were then incubated in the monoclonal antibody solution (0.1 mg/ml; in TTBS with 10% goat serum), washed as above, and incubated with anti-mouse IgG-alkaline phosphatase solution (1:1,000, Sigma Chemical Co., St. Louis, Mo., #A-5153; in TTBS with 2% goat serum). Following washing, the conjugates were visualized using NBT-BCIP substrate (Bio-Rad Laboratories, Inc., #170–6432). All blots were characterized based on the strength of the immunochemical reaction, i.e., strong, moderate, weak, or negative.

Using western blot analysis, the primary antigen for both monoclonal antibodies was determined to be vitellin. The HZE-1 antibody reacted strongly with *H. zea* vitellin, while antibody HVE-1 reacted strongly with the vitellin of *H. virescens*. Moreover, western blots of the SDS-PAGE gels with the HZE-1 antibody revealed that its determinant was no longer recognizable after dissociation of the holoprotein (Table 3) indicating that determinant recognition necessitated an intact holoprotein. Conversely, the HVE-1 antibody recognized its determinant, which was located on the large vitellin apoprotein, apoVn-I, following denaturing electrophoresis.

The results of the western blot analysis of the egg homogenates from five heliothine species and three non-heliothine noctuids are shown in Table 3. The HZE-1 antibody cross-reacted strongly with *H. armigera* vitellin and moderately with *H. punctigera* vitellin, but it did not react with the vitellins from *H. virescens*, *H. subflexa*, or the non-heliothine noctuids (*S. frugiperda*, *T. ni*, *A. gemmatalis*). Conversely, the HVE-1 antibody cross-reacted strongly with the native vitellins from all heliothine egg homogenates. After denaturing electrophoresis, the HZE-1 antibody did not recognize vitellin from any species, whereas the HVE-1 antibody recognized the apoVn-I from all the heliothines, although it only moderately recognized the large apoproteins of the old world heliothines, *H. armigera* and *H. punctigera*.

The results of the tests against larva, pupa, and adult preparations are also shown in Table 3. Neither antibody cross-reacted with native proteins from either the larval or pupal stages of *H. zea* and *H. virescens*. A very weak cross-reaction was seen with HZE-1 to a high-molecular weight polypeptide in the hemolymph of fifth instar *H. zea* following SDS-PAGE. Blots of hemolymph from adults ranging from day-0 to day-7 post-eclosion indicated that both antibodies recognized a protein migrating slightly slower than vitellin, with the protein being recognized strongly by the HZE-1 antibody and moderately by the HVE-1 antibody. Additional western blots indicated that the immunoreactive protein was solely present in the hemolymph from female and not male adults. Since vitellogenin, the precurser for vitellin (Hagedorn and Kunkel, 1979; Kunkel and Nordin, 1985; Raikhel and Dhadialla, 1992; all ibid) appears in the hemolymph of adult *H. zea* females within 8–10 hours after eclosion (Satyanarayana et al., 1992) and, in *M. sexta*, is known to migrate more slowly than vitellin on electrophoretic gels (Imboden and Law, 1983, Insect Biochem., 13:151–162), we conclude that this immunoreactive protein is vitellogenin. Thus, the antibodies HZE-1 and HVE-1 recognized the vitellins from *H. zea* and *H. virescens*, respectively, and the precurser of vitellin, vitellogenin, but not insect proteins from any other stages tested.

It is understood that the foregoing detailed description is given merely by way of illustration and that modifications and variations may be made therein without departing from the spirit and scope of the invention.

TABLE 2

Results of squashblot assays on field-collected eggs.

| Species | *H. zea* | | *H. virescens* | |
|---|---|---|---|---|
| Locality | + | − | + | − |
| Georgia | 135 | 1 | 0 | 84 |
| Mississippi | — | — | 0 | 42 |
| Tennessee | — | — | 0 | 24 |
| Texas | — | — | 0 | 60 |

—, not available

TABLE 3

Response of antibodies to various samples following western blotting

| | | ANTIBODY | | | |
|---|---|---|---|---|---|
| SAMPLE | | HZE | | HVE | |
| Species | Stage | Native | SDS | Native | SDS |
| *H. zea* | Egg | +++ | − | +++ | +++ |
| | Larval | − | − | − | + |
| | Pupal | − | NT | − | NT |
| | Adult | | | | |
| | Female | +++ | NT | ++ | NT |
| | Male | − | NT | − | NT |
| *H. virescens* | Egg | − | − | +++ | +++ |
| | Larval | − | NT | − | NT |
| *H. subflexa* | Egg | − | − | +++ | +++ |
| *H. armigera* | Egg | +++ | − | +++ | ++ |
| *H. punctigera* | Egg | ++ | − | +++ | ++ |
| *S. frugiperda* | Egg | − | NT | − | NT |
| *T. ni* | Egg | − | NT | + | NT |
| *A. gemmatalis* | Egg | − | NT | + | NT |

I claim:

1. A hybridoma cell line which produces and secretes monoclonal antibody HZE-1, which specifically binds to vitellin of the corn earworm, *Helicoverpa zea*, but does not bind to vitellin of the tobacco budworm, *Heliothis virescens* (Fabricus).

2. Monoclonal antibody HZE-1 produced by the cell line of claim 1.

3. A method of detecting eggs of the corn earworm, *Helicoverpa zea*, which comprises:
   a) providing a sample of an insect egg;
   b) subjecting said egg to an immunosorbent assay using the monoclonal antibody HZE-1 produced by the cell line of claim 1.

4. The method of claim 3 wherein said immunosorbent assay comprises:

TABLE 1

Results of sqashblot assays on insectary-reared eggs

| Species | *H. Zea* | | *H. virescens* | | *H. subflexa* | | *S. frugiperda* | | *T. ni* | | *A. gemmatalis* | |
|---|---|---|---|---|---|---|---|---|---|---|---|---|
| Source | + | − | + | − | + | − | + | − | + | − | + | − |
| Eggs sheets | 1,096 | 5 | 1 | 1,052 | 0 | 84 | 0 | 84 | 0 | 84 | 0 | 84 |
| Cotton leaves | 24 | 0 | 0 | 24 | — | — | — | — | — | — | — | — |
| Soy leaves | 80 | 0 | 0 | 80 | — | — | — | — | — | — | — | — |
| Infertile | 64 | 0 | — | — | — | — | — | — | — | — | — | — |

—, not tested a) transferring said egg to the surface of a solid substrate;

b) crushing said egg and allowing the crushed egg to bind to said substrate;

c) contacting said crushed egg with said monoclonal antibody HZE-1 under conditions which allow vitellin in eggs of *Helicoverpa zea* to bind to said monoclonal antibody;

d) washing said substrate to remove any unbound monoclonal antibody from said substrate; and e) detecting any of said monoclonal antibody HZE-1 retained on said substrate.

5. The method of claim 4 wherein said substrate comprises a membrane.

6. The method of claim 5 wherein said membrane comprises a nitrocellulose membrane.

7. A kit for detecting eggs of the corn earworm, *Helicoverpa zea*, comprising the monoclonal antibody HZE-1 produced by the cell line of claim 1.

8. The kit of claim 7 further comprising a detection reagent effective for detecting said monoclonal antibody.

* * * * *